United States Patent
Miyazaki et al.

(10) Patent No.: US 6,245,354 B1
(45) Date of Patent: Jun. 12, 2001

(54) DRUG DELIVERY SYSTEM USING GALACTOXYLOGLUCAN

(75) Inventors: Shozo Miyazaki, Sapporo; Mayumi Shirakawa, Suita; Kazuhiko Yamatoya, Urawa, all of (JP)

(73) Assignee: Dainippon Pharmaceutical Co., Ltd., Osaka-fu (JP)

( * ) Notice: Subject to any disclaimer, the term of this patent is extended or adjusted under 35 U.S.C. 154(b) by 0 days.

(21) Appl. No.: 09/125,262
(22) PCT Filed: Feb. 13, 1997
(86) PCT No.: PCT/JP97/00381
 § 371 Date: Aug. 12, 1998
 § 102(e) Date: Aug. 12, 1998
(87) PCT Pub. No.: WO97/29777
 PCT Pub. Date: Aug. 21, 1997

(30) Foreign Application Priority Data

Feb. 13, 1996 (JP) .................................. 8-050864

(51) Int. Cl.[7] .................................................. A61K 9/22
(52) U.S. Cl. .................. 424/468; 424/400; 424/464; 424/489; 424/493; 252/312; 514/777; 514/964
(58) Field of Search ................ 424/400, 489, 424/464, 468, 493; 252/312

(56) References Cited

U.S. PATENT DOCUMENTS

| | | | |
|---|---|---|---|
| 4,668,232 | 5/1987 | Cordes et al. | 604/897 |
| 4,861,760 | 8/1989 | Mazuel et al. | 514/54 |
| 5,234,825 | * 8/1993 | McCleary et al. | 435/101 |
| 5,488,105 | * 1/1996 | Uno et al. | 536/128 |
| 5,700,397 | * 12/1997 | Maeda et al. | 252/312 |
| 6,087,324 | * 7/2000 | Igari et al. | 514/2 |

FOREIGN PATENT DOCUMENTS

| | | |
|---|---|---|
| 0640622 A1 | * 2/1994 | (EP) . |
| 61-155321 | 7/1986 | (JP) . |
| 63-215620 | 9/1988 | (JP) . |
| 63-238017 | 10/1988 | (JP) . |
| 5-39306 | 2/1993 | (JP) . |
| WO97/29777 | * 8/1997 | (JP) . |

OTHER PUBLICATIONS

S. Miyazaki et al. "Pluronic F–127 Gels as a Vehicle for Topical Administration of Anitcancer Agents", Chem. Phar. Bull., vol. 32, No. 10, pp. 4205–4208, 1984.

* cited by examiner

Primary Examiner—Thurman K. Page
Assistant Examiner—Lakshmi Channavajjala
(74) Attorney, Agent, or Firm—Wenderoth, Lind & Ponack, L.L.P.

(57) ABSTRACT

The present invention relates to a pharmaceutical sustained release preparation prepared by using as a sustained release ingredient a partial degradation product of the galactose of a galactoxyloglucan and a method for sustained releasing of a drug thereby. In more detail, it relates to a pharmaceutical sustained release preparation, wherein the sustained release of a drug is effected by utilizing the thermally reversible gel characteristics of the galactose-partial degradation product, which is produced by partial removal of the galactose on the side-chain of a galactoxyloglucan with an enzyme.

8 Claims, 5 Drawing Sheets

DRUG DELIVERY SYSTEM USING GALACTOXYLOGLUCAN

TECHNICAL FIELD

The present invention relates to a drug delivery system using a galactoxyloglucan, that is, to a drug sustained release preparation containing as a sustained release ingredient a partial degradation product of the galactose moiety of a galacto-xyloglucan and a method for the sustained release of a drug thereby. More particularly, the present invention provides a drug sustained release preparation which can gradually release the drug in biobody by utilizing thermally reversible gel (or thermoreversible gel) behavior of the galactose-partial degradation product of a galactoxyloglucan, which is produced by partially removing a galactose moiety on the side-chain from a galactoxyloglucan with an enzyme, and also provides a method of gradually releasing a drug by using the galactose-partial degradation product of a galactoxyloglucan.

PRIOR ART

The so-called drug delivery system (abbreviated as DDS), that is a technique for maintaining a constant blood level of a drug for a long period of time by administrating of a drug into body, or for maintaining an optimal concentration of a drug in the target organ specifically and further for a long period of time, is important in order to enhance the effect of the drug, and to diminish a side effect so as to use the drug safely. A pharmaceutical preparation defined as a sustained release preparation is known as one of such techniques, and the development of a sustained release preparation being capable of controlling the release of drugs at the most suitable release rate and concentration is important no less than the development of a new drug.

Various new forms of a pharmaceutical preparation are known as such a drug sustained release preparation, which include forms approached from technological aspect, such as those utilizing a thin membrane of a polymer or utilizing a deformated surface of a solid material and further forms approached from biological aspect, such as those utilizing as a carrier a liposome, an emulsion or a polylactic acid.

As a pharmaceutical preparation being capable of sustaining release of a drug, a hydrogel preparation using various hydrogels as a sustained release ingredient has been proposed, for instance, a hydrogel preparation comprising a core composed of a drug and a water-soluble polymer, and an outer layer of a base material comprising a water-soluble polymer (JP-A-63-215620), and a composite drug prepared by incorporating a peptide into a polysaccharide (JP-A-5-38635). Furthermore, it is reported to use a suppository using as a sustained release ingredient, Pluronic, a polyoxyethylene-polyoxypropylene copolymer which is in the form of a sol at a low temperature but is gelled at a body temperature [S. Miyazaki et. al., Chem. Pharm. Bull., 32, 4205 (1984)].

The conventional attempts using a polymer having gelling property as a gel base for a drug (a sustained release ingredient) have some problems such as a difficulty of the infusion into the body or being painful due to high viscosity in any dosage form such as oral administration, rectal administration with a suppository etc. or injection.

A gel base for DDS, which maintains a suitable shape in a body and enables to exhibit the sustained release properties, is desired to have the characteristic that it has a low viscosity and is liquid or a sol when infused, and it is thickened and gelled at around the body temperature. The above-mentioned synthetic polymer, Pluronic, is known as such a gel base, but it must be used in a high concentration such as 20 to 30% for gelation. On the other hand, for oral administration, the dosage shall be at the most about several hundreds of mg per kg in view of safety, and the amount in the safe range is not necessarily suitable to the desired sustained release preparation in the scope of safety.

An object of the present invention is to provide a sustained release preparation using a natural polysaccharide which is safe for a body as a gel base (a sustained release ingredient) for DDS and a method for effecting sustained release of a drug.

SUMMARY OF THE INVENTION

The gel base (a sustained release ingredient) useful for DDS have preferably the following characteristics; 1) it is originated from nature to be safeful for the body, 2) it can be gelled even in a low concentration, 3) it has a low viscosity at room temperature and is liquid or a sol when infused and it is thickened and gelled at a body temperature within the body. The present inventors have intensively studied to produce a gel base satisfying the above characteristics from natural polysaccharides which are safe for a body, and as a result, have found that the partial degradation product of the galactose moiety of a galactoxyloglucan, which is produced by removing a part of galactose moieties from a galactoxyloglucan (hereinafter, it is optionally referred to as a merely as "galactose-partial degradation product"), is useful as a gel base. That is, the present invention provides a drug sustained release preparation which is produced by incorporating of a drug into the galactose-partial degradation product to be used as a gel base. The present invention provides also a method of controlling release of a drug by incorporating the galactose-partial degradation product as a sustained release ingredient into a drug-containing preparation.

DISCLOSURE OF THE INVENTION

Figure 1:
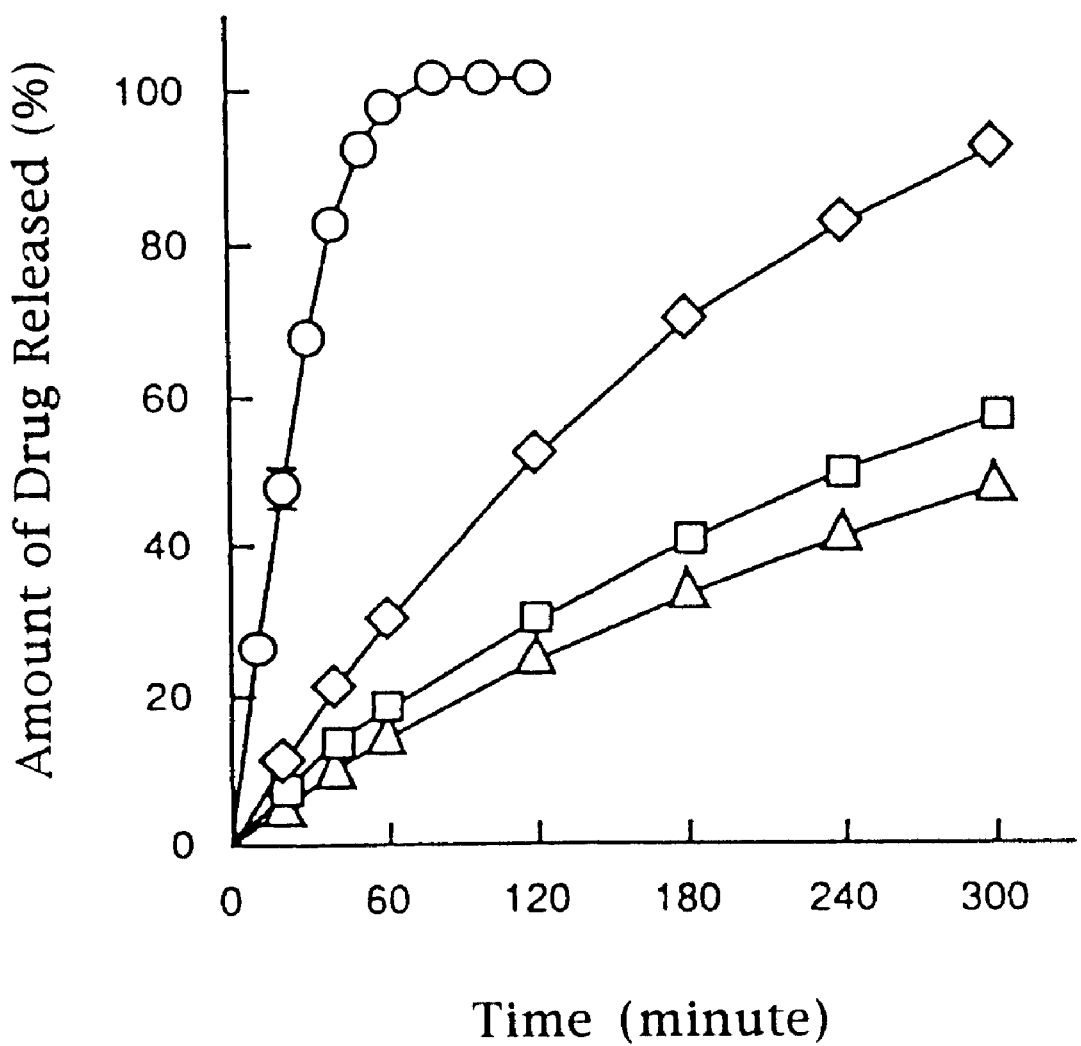
FIG. 1 shows a result of a test of release of a drug at 37° C. from an indomethacin suppositories which are prepared using a 0.5 W/V %, 1.0 W/V %, or 2.0 W/V % aqueous solution of the galactose-partial degradation product (pH 7.2, phosphate buffer) as well as from a commercially available indomethacin suppository. The vertical axis represents the amount of drug released (%), and the horizontal axis represents time (minute). The symbol —○— represents the case of the commercially available indomethacin suppository, and the symbols —◇—, —□— and —△— represent the cases of the indomethacin suppositories prepared from the 0.5 W/V %, 1.0 W/V %, and 2.0 W/V % aqueous solutions of the galactose-partial degradation product, respectively.

The sustained release preparation of the present invention includes a partial degradation product of the galactose moiety of a galactoxyloglucan as an ingredient for effecting sustained release of a drug, and is prepared by using the galactose-partial degradation product as a gel base, i.e. by incorporating a drug into said gel base and being formed into the desired dosage form in admixture with a conventional pharmaceutically acceptable carrier or diluent in a usual manner.

When the preparation of the present invention is administered, the galactose-partial degradation product incorporated as a drug sustained release ingredient is gelled due to the body temperature and to form a matrix, wherein the drug is embraced, and thereby the release of drug is controlled so as to gradually release it, and as a result the desirable drug level is maintained for a long period of time.

The present invention is explained in more detail below.

The partial degradation product of the galactose moiety of a galactoxyloglucan of the present invention mean the compound, wherein galactose moiety on the side chain are partially removed from a galactoxyloglucan and may be abbreviated as the galactose-partial degradation product.

Galactoxyloglucan is a constitute component of a cell wall (a primary wall) of a higher plant such as dicotyledon, monocotyledon and it exists as a reserve polysaccharide of a part of plant seeds. Galactoxyloglucan consists of saccharides selected from glucose, xylose, and galactose, wherein the main chain consists of $\beta$-1,4 bonded glucose, and the side chain consists of xylose and further galactose bonds to the xylose. The galactoxyloglucan per se usually does not gel, but it gels in the presence of a saccharide, an ion, or an alcohol. However, it has recently been reported that when the galactose on the side chain of a galactoxyloglucan is removed in a ratio of 30–55%, it induces thermally reversible gel characteristics, that is, it behaves reversibly gelation by heating and forming of sol by cooling (Shirakawa et. al., Annual Meeting of Japan Society for Bioscience, Biotechnology, and Agrochemistry, 1995, JP-A-8-283305). However, it has not been known to be useful as a gel base for DDS.

Galactoxyloglucan used in the present invention includes galactoxyloglucan originated from any plants; for instance, seeds of tamarind, jatoba and nasturtium, cereals such as soybean, greenbean, kidney beans, rice and barley or skin of fruits (e.g. apple). The most preferable one is a galactoxyloglucan obtained from tamarind seed in the pea family because the tamarind seed is the most easily available and has a large content thereof.

The method of the partial removal of the galactose moiety from a galactoxyloglucan is, for instance, a hydrolysis with a diluted inorganic acid such as diluted hydrochloric acid, a pyrolysis and an enzymatic hydrolysis, but the former two methods are unsuitable because the main chain and a xylose on the side chain are simultaneously cleaved. Preferred method is an enzymatic hydrolysis, particularly an enzymatic hydrolysis using a $\beta$-galactosidase which can cleave galactose specifically. The enzymatic hydrolysis can be carried out under mild conditions, and further can be carried out the partial removal of galactose on the side chain selectively depending to the conditions. The $\beta$-galactosidase includes any product obtained from plants or microorganisms, but preferrable one is an enzyme originated from the microorganisms such as *Aspergillus orizae*, or *Bacillus circulans*, or an enzyme in the seed containing galactoxyloglucan. Commercially available enzyme products contain occasionally cellulase or isoprimeverose-producing enzyme and hence, if necessity, the enzymes may be purified to remove those enzymes. The purification may be carried out, for instance, various kinds of chromatography utilizing differences in the physical properties such as ion-exchange characteristics, hydrophobic properties, affinity etc., such as ion-exchange chromatography and affinity chromatography.

The method of the partial removal of the galactose moiety of a galactoxyloglucan using enzyme is usually carried out by treating an aqueous solution of the substrate galactoxyloglucan with a $\beta$-galactosidase under the optimum conditions such as the optimal reaction temperature, pH and concentration, and in this case the galactose may be removed at a constant ratio corresponding to the reaction time. For instance, in the case of a 2% substrate concentration, it may be carried out under a 0.05% enzymatic concentration, pH 5~6 and reaction temperature 50~55° C . In the enzymatic reaction, the galactose on the side chain is removed partially with progressing of the reaction, and where the removal ratio of a galactose reaches to about 30%, the reaction solution is rapidly thickened and gelled. Where the removal ratio of galactose is in the range of 30 to 55%, the galactose-partial degradation product has reverse thermal gelation characteristics, whereby it is gelled by heating and forms sol by cooling. Where the removal ratio of galactose is less than 30%, it does not gel, and on the other hand, where the ratio is over 55%, it forms a strong gel.

Since the gel base for DDS is required to be soluble in water and to gel at around the body temperature, the galactoxyloglucan used in the present invention has a removal rate of galactose in the range of 30 to 55%, preferably in the range of 35 to 50%. The galactose-partial degradation product is usually used in the form of an aqueous solution, and the concentration of the solution varies depending on the removal ratio of the galactose and on the desired dosage form, but preferably is in a low concentration such as 0.5~3.0 W/V %.

The gel base used in the present invention has thermally reversible gel characteristics at a low concentration and hence is usable as a base for the material for controlling release of a drug or a base for a preparation suitable for staying a drug in the body. Besides, the gel base is a galactoxyloglucan originated from natural products, and hence it is safety to biobodies.

The preparations prepared by using the galactose-partial degradation product of the present invention as a gel base can release the drug gradually and the release of drug can be controlled by selecting adequately the removal ratio of galactose in the galactose-partial degradation product and the concentration thereof.

The sustained release preparation of the present invention is prepared in various dosage forms according to the administration routes; for instance, preparations for oral administration such as tablets, capsules, granules, liquid preparations or jelly; suppositories for rectal absorption; suppositories for vaginal route, patches suitable for absorptions via percutaneous or mucous membrane route; cataplasms; preparations applicable into oral cavity (troche); dental preparations; liquid preparations or jelly for intraperitoneal administration; injections for intravenous, intramuscular or subcutaneous injection; eye drops; or nasal drops. These preparations may be prepared by conventional methods [cf, for instance "Recent Techniques for Preparation and their Application", I. Utsumi etc., Medical Journal, page 157–159 (1983)]. Tablets may be prepared by mixing the galactose-partial degradation product with a drug and conventional carriers for tablets, followed by tabletting the mixture directly with a tabletting machine to give the desired tablets. Suppositories and preparations for intraperitoneal administration are prepared by preparing an aqueous solution in an adequate concentration (0.5~3.0 W/V %) of the galactose-partial degradation product in a cold water, adding thereto a drug and kneading the mixture to give a liquid preparation. This liquid preparation can be administered by infusing into the rectum or the abdominal cavity with an infusion syringe, whereby the galactose-partial degradation product thus infused is gelled by the body temperature and the preparation is stayed in the rectum or in the abdominal cavity. Besides, such a liquid preparation may be previously gelled by heating in a molding vessel, and the resulting gel preparation may be inserted into the rectum or the abdominal cavity. The patches suitable for the percutaneous or mucous membrane absorptions are prepared by mixing the galactose-partial degradation product and a drug and optionally other additives, and spreading the mixture onto a support cloth in an usual manner. In all methods as mentioned above, the products can be controlled so that the contents are gelled at around the body temperature. Since the concentration suitable for gelling the galactose-partial degradation product is in a low concentration range such as 0.5 to 3.0 W/V %, these preparations may be formulated so as to be within such a concentration range. The galactose-partial degradation product may be used alone as a sustained release ingredient with a drug, but may be used together with other conventional additives such as hydrophilic bases (e.g. polyethylene glycol, sorbitol, dextran etc.), polymers (e.g. polyethylene oxide, methyl cellulose, CMC etc.), surfactants (e.g. higher fatty acid esters), and excipients.

The drugs used in the present invention are not limited in particular, so long as aiming at sustaining release, and include various kinds of drugs; for instance, anti-inflammatory agents, antipyretics, antispamodics, analgesics, antituberculosis drugs, drugs for circulatory organs, antipsychotic drugs, antihistaminics, vitamins, antiarthritics, hypnotic sedatives, carcinostatic agents, antineoplastic drugs, decongestants, antidiabetics, diuretics, bronchodilators, antitussives, antiarrhythmics, surface anesthesia drugs, antiepileptics, steroids, drugs for digestive organs, central nervous system drugs, anti-hyperlipidemics, antibiotics, diagnostic drug, bowel movement improvers, antiallergic drugs, agents for applying to epidermics, and ophthalmic drugs.

BEST MODE FOR CARRYING OUT THE INVENTION

The present invention is illustrated by means of reference examples and examples but is not limited thereto.

Reference Example 1

Preparation of the partial degradation product of the galactose moiety of a galactoxyloglucan:

Galactoxyloglucan originated from tamarind seed (Trade name: "GLYROID", manufactured by DAINIPPON PHARMACEUTICAL CO., LTD.) (120 g) was dissolved in water (4 kg) with vigorous stirring. The mixture was maintained at 55° C. and then adjusted to pH 6 using trisodium citrate, followed by addition of β-galactosidase (Trade name: "Biolacta N5", manufactured by DAIWA KASEI CO., LTD.) (3.6g), and the mixture was reacted with stirring for 16 hrs. After the enzyme was inactivated by heating at 95° C. for 30 minutes, the mixture was cooled to room temperature and thereto was added an equal amount of ethanol and then the mixture was allowed to stand for 1 hr. After the resulting precipitates were collected by filtration with suction and dried with a blower drier, the precipitates were pulverizated and passed screen to give a powder of the galactose-partial degradation product (the removal ratio of galactose: about 44%, 103 g). The removal ratio of galactose was calculated from an amount of free galactose measured by high performance liquid chromatography (a connected column: Shodex lonpak KS 805+KS802).

Reference Example 2

The gelling properties of the galactose-partial degradation product:

The powdery of the galactose-partial degradation product obtained in Reference Example 1 (the removal ratio of galactose: about 44%) was dispersed and dissolved in a purified water or a phosphate buffer (pH 7.2) with stirring under ice-cooling to prepare 0.5 W/V %, 1.0 W/V %, 2.0 W/V % and 3.0 W/V % solutions. Such partial degradation products were gelled at a low concentration (1.0 W/V % or more), and a 2.0 W/V % aqueous solution of the partial degradation product was gelled at about 20° C. Besides the each aqueous solution was observed the gelling properties (sol/gel behavior), under ice-cooling or at 37° C. respectively. The results are shown in Table 1.

TABLE 1

The gelling properties of the galactose-partial degradation product

| Concentration of the aqua. solutions W/V% | Solvents | Temperature (° C.) | Sol/Gel behavior |
|---|---|---|---|
| 1.0 | Purified water | ice-cooling | Sol |
|  |  | 37 | Gel |
| 2.0 | Purified water | ice-cooling | Sol |
|  |  | 37 | Gel |
| 3.0 | Purified water | ice-cooling | Sol |
|  |  | 37 | Gel |
| 0.5 | Phosphate buffer, pH 7.2 | ice-cooling | Sol |
|  |  | 37 | Sol |
| 2.0 | Phosphate buffer, pH 7.2 | ice-cooling | Sol |
|  |  | 37 | Gel |

Example 1

Release properties of drugs in the gel suppository consisting of indomethacin and the galactose-partial degradation product:

An appropriate amount of the powdery galactose-partial degradation product obtained in Reference Example 1 was added in portions to a phosphate buffer (pH 7.2) with stirring under ice-cooling and stirred for about 1 hr at about 4500 rpm to prepare the 0.5 W/V %, 1.0 W/V % and 2.0 W/V % aqueous solutions respectively. Test samples were prepared by dissolving indomethacin (25 mg, manufactured by SIGMA CO.) as a controlled drug into the above each aqueous solution (3 ml) (the drug concentration: 0.83 W/V %). These test samples were gelled by heating to 37° C. Release of a drug was tested as to the drug (25 mg)-containing test samples. An indomethacin suppository (Trade name: "Hisamitsu IND" manufactured by HISAMITSU PHARMACEUTICAL CO., INC.) was used as a controlled sample.

The drug-release test was carried out by using a testing apparatus for release test on suppository (manufactured by TOYAMA INDUSTRY CO, LTD., TMS-103) at 37° C. That is, a phosphate buffer (pH 7.2, 300 ml) was used as a release solution, and the above test sample and the phosphate buffer (pH 7.2, 3 ml) were placed into the cell for suppository equipped with a membrane filter (the pore size: 3.0 μm) and the test was carried out at 37±0.1° C. The drug concentration in the release solution was measured by a spectrophotometric method (266 nm) with the lapse of time at a speed of stirring of 100 rpm and a velocity of shaft rotation of 25 rpm. The amount of drug in the released solution to that of the drug to be contained in the specimen suppository was calculated as the amount of drug released (%). The results were shown in FIG. 1.

As is clear from FIG. 1, in the suppository on the market (—○—) the drug was released in about 100% within 1hr, and on the other hand, in the gel suppositories of the galactose-partial degradation product (0.5 W/V % (—◇—), 1 W/V % (—□—) and 2 W/V % (—△—)) the release rate was less than 30% even after 1hr and thus the release rate of a drug from the gel preparations suggests a sustained release. In particular, the gel suppositories prepared from the 1 W/V % and 2 W/V % aqueous solutions exhibited excellent sustained release properties.

Example 2

Release of a drug in the tablet consisting of diltiazem hydrochloride and the galactose-partial degradation product:

Diltiazem hydrochloride (30 mg) on the market [manufactured by WAKO PURE CHEMICAL INDUSTRIES, LTD.] and the galactose-partial degradation product (75 mg) obtained in Reference Example 1 were uniformly mixed, and the mixture was tabletted directly by a tabletting machine for potassium bromide (pressure: 200 kg/cm$^2$ for 2 minutes) to prepare a tablet (diameter: 10 mm, weight: 105 mg). The drug-relase test of the diltiazem hydrochloride (30 mg)-containing tablet was carried out by the dissolution test as defined in The Pharmacopoeia of Japan XII (a rotating basket method) using as a test solution the first solution (pH 1.2, 37° C.) in the disintegration test in the Pharmacopoeia of Japan XII at a rotation of 150 rpm. A fixed amount of the test solution was collected with the lapse of time and the absorbance thereof was measured at 237 nm and then the concentration of a drug was calculated. Diltiazem hydrochloride on the market was used as a controlled drug. The amount of the drug in the test solution to that of the drug contained in the specimen tablet was calculated as the amount of drug released (%). The results are shown in FIG. 2.

Figure 2:
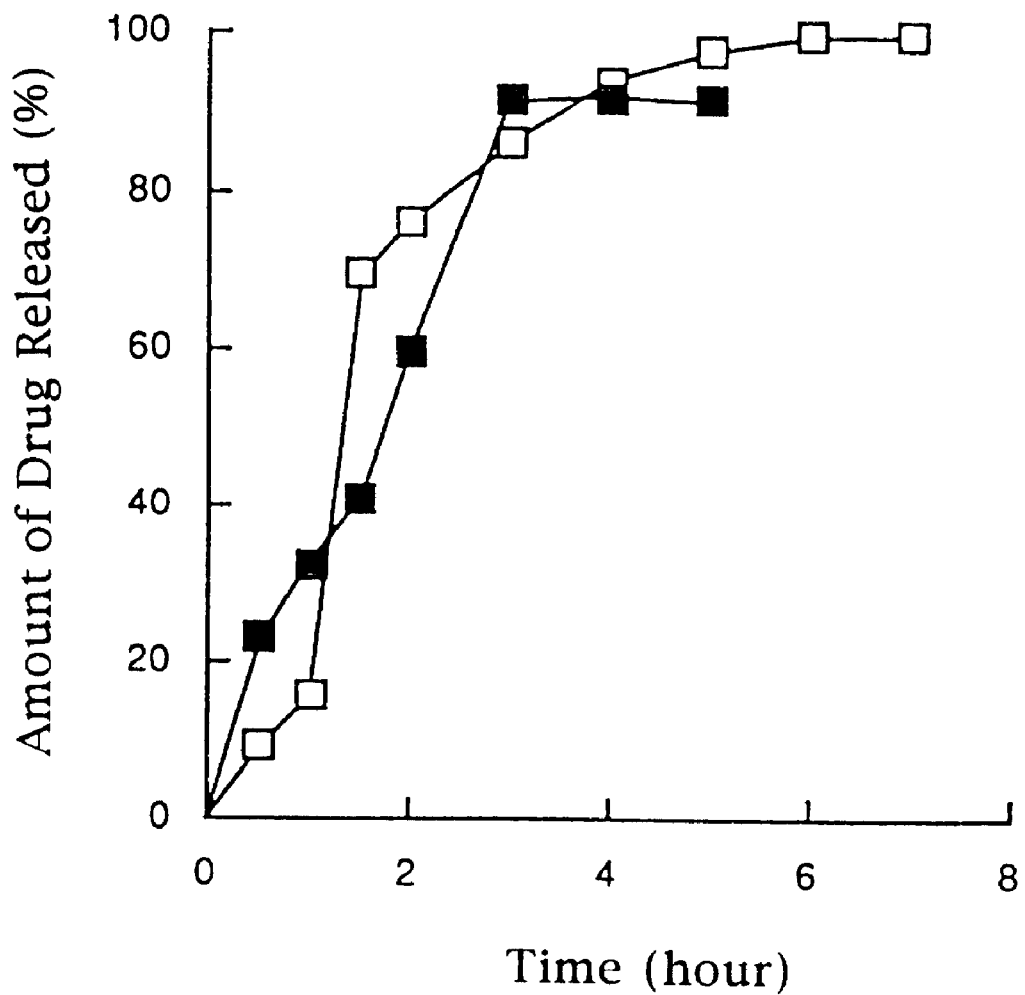
FIG. 2 shows a result of a test of release of a drug at 37° C. from a tablet comprising diltiazem hydrochloride and the galactose-partial degradation product. As a control, a commercially available diltiazem hydrochloride tablet was used. The vertical axis represents the drug release ratio (%), and the horizontal axis represents time (hour). The symbol —□— represents the case of the commercially available tablet, and the symbol —■— represents the case of the tablet containing the galactose-partial degradation product.

As is clear from FIG. 2, the drug release of the tablet in the present invention (—■—) exhibited the same behavior as that of tablet on the market (—□—).

Example 3

Test of absorption of drug through rectal mucous membrane in rabbit:

1) Behavior of the gel suppository containing no drug of the present invention in rectum of rabbit:

A liquid suppository (3 ml), a 2.0 W/V % aqueous solution of the galactose-partial degradation product obtained in Example 1 which contained fluorescein sodium, was administrated by infusion into the rectum of a fasted male Japanese white rabbit (body weight: 3.0–4.0 kg) (allowing to take water freely) at a distance of about 2 cm from the anus with a disposyringe connected to a silicone tube (about 3 cm). The state of distribution of the suppository was photographed by UV irradiation after 1, 3 and 6 hrs. As a result, it was observed that every gel suppositories existed in the rectum in the state of a gel.

Figure 3:
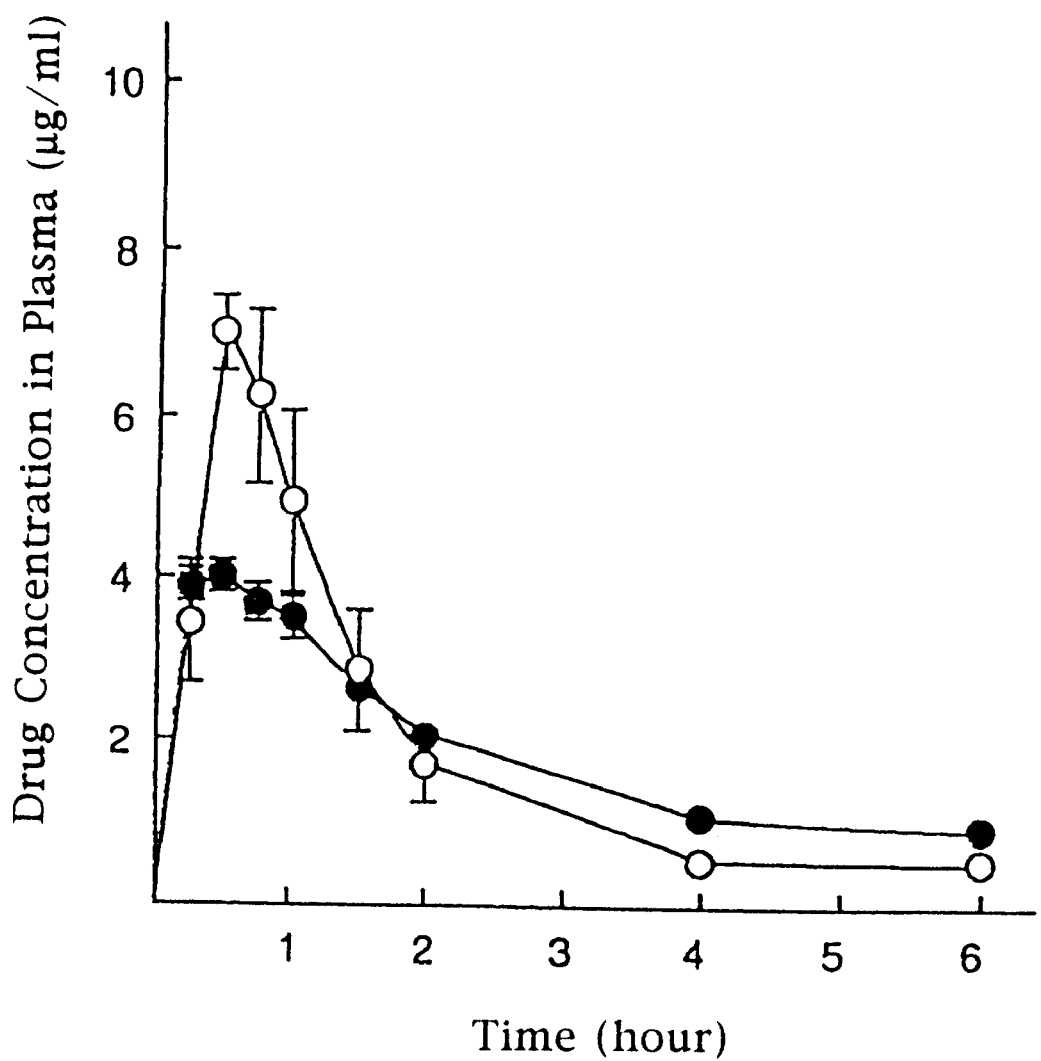
FIG. 3 shows a result of a test for absorption of a drug through the rectal mucous membrane in rabbits as to an indomethacin suppository incorporated with the galactose-partial degradation product and a commercially available indomethacin suppository. The vertical axis represents the drug concentration in the plasma ($\mu$g/ml), and the horizontal axis represents time (hour). The symbol —○— represents the case of the commercially available indomethacin suppository, and the symbol —●— represents the case of the indomethacin suppository prepared using a 2.0 W/V % aqueous solution of the galactose-partial degradation product.

2) Test of absorption of a drug in rectal mucous membrane from the drug-containing gel suppository of the present invention in rabbit:

An indomethacin suppository on the market (Trade name: "Hisamitsu IND", manufactured by HISAMITSU PHARMACEUTICAL CO., INC.) was administered into the rectum of male Japanese white rabbits fasted for 36 hrs (body weight: 3.0–4.0 kg, four rabbits) (allowing to take water freely). On the other hand, the indomethacin-containing gel suppository (as a sol, 3 ml) consisting of a 2.0 W/V % aqueous solution of the galactose-partial degradation product obtained in Example 1 was administered by infusion into the rectum of the rabbits at a distance of about 2 cm from an anus thereof with a disposyringe connected to silicone tube (about 3 cm). In every cases, a blood sample (about 1 ml) was collected from the ear vein of the rabbit with the lapse of time and a concentration of indomethacin in the plasma was measured by HPLC (high performance liquid chromatography) method. The results are shown in FIG. 3. Besides, Table 2 indicates pharmacokinetics parameters obtained from the change of the blood concentration shown in FIG. 3.

TABLE 2

Comparison of the pharmacokinetics parameters

| Pharmaceutical preparations | n (number of rabbit) | Tmax (hr) | Cmax (μg/ml) | AUC(0~6 hr) (μg · hr/ml) |
|---|---|---|---|---|
| Suppository on the market | 4 | 0.5 | 8.59 ± 0.49 | 11.87 ± 0.62 |
| Suppository of the present invention | 4 | 0.5 | 3.54 ± 0.34* | 11.36 ± 0.96 |

Significant difference test: $*p < 0.01$

As is clear from FIG. 3 and Table 2, both the suppository on the market and the gel suppository of the present invention showed rapid absorption. $T_{max}$ (a time reached to a maximum plasma concentration) being 0.5 hour, but $C_{max}$ (a maximum plasma concentration) of the gel suppository of the present invention was a half of that of the suppository on the market and further the gel suppository of the present invention showed more sustained blood concentration than that of the suppository on market. Besides, as to AUC (area under the curve of the correlation of the blood concentration-time) indicating a bioavailavility, both suppositories showed almost the same values. The above results suggest that the administration of the gel suppository of the present invention enables to maintain the effective blood concentration of drug for a long time and to have a durability in the amount of drug released. Thus, administration of the gel suppository of the present invention enables to diminish the side effect of drugs.

3) Irritation to the rectal mucous membrane by the drug-containing gel suppository of the present invention in rabbit:

Gel suppositories of the present invention (the 2.0 W/V % aqueous solution of the galactose-partial degradation product obtained in Example 1) which contained indomethacin or not was each administered into the rectum of rabbits, and a histophthological test was done for the rectal mucous membrane after 6 hrs, but no abnormal phenomenon was observed on the rectal tissue and no irritation onto the rectal mucous membrane was found.

The above results suggest the gel suppository of the present invention is useful as a base for preparing a sustained release preparation suitable for rectal administration.

Example 4

For the purpose of the treatment of various tumors such as a peritoneal, or carcinomatous peritonitis there has hitherto been used mitomycin C, an anti-cancer agent. However since the mitomycin C administered into the abdominal cavity is rapidly transferred to a systemic circulation, it can not exhibit sufficient therapeutic effects. Then, in order to prolong the retention time of mitomycin C in the abdominal cavity, it was tried to apply the drug-containing gel preparation of the present invention, which test was carried out in rats by intraperitoneal administration of the preparation.

A test by intraperitoneal administration in rats:

Male Wistar rats fasted for 18 hours (allowing to take water freely) were used.

1) Gelling properties of the gel preparation containing no drug of the present invention in the abdominal cavity:

A 1.5 W/V % aqueous solution of the galactose-partial degradation product obtained in Example 1 (4 ml) in the form of a sol, which was colored with bromothymol blue, was administered by infusion into the abdominal cavity.

Then the state of distrubution of the preparation was observed for 6 hrs. As a result, it already became gelation in 15 minutes after administration. Thus, it was found that the solution administered into the abdominal cavity gelled rapidly. Besides, the state of gelation was kept after 1 hour or even after 6 hrs.

2) A test by intraperitoneal administration of the drug-containing gel preparation of the present invention into rat:

A 1.5 W/V % aqueous solution (4 ml) of the galactose-partial degradation product containing mitomycin C (5 mg/kg) was administered by infusion into the abdominal cavity of rat, and the concentration of mitomycin C in plasma or in ascites was measured with the lapse of time by HPLC method.

As a control, an equal amount of an aqueous solution containing mitomycin C (5 mg/kg) was used. The measurement of the concentration of drug in ascites was done using as an artificial ascites a solution which was prepared, when measured, by infusing an isotonic sodium chloride solution (5ml) into the abdominal cavity and re-sucking. The results are shown in FIG. 4 and FIG. 5.

Figure 4:
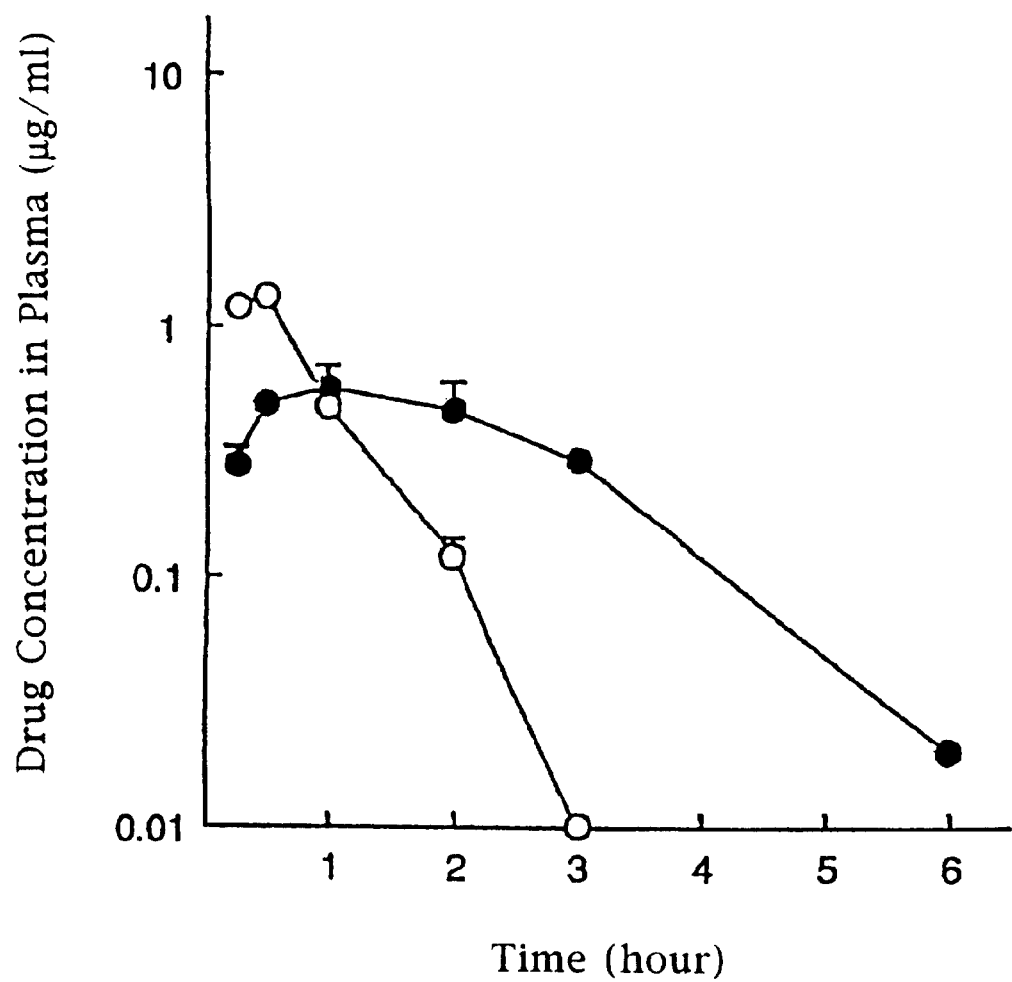
FIG. 4 shows the change of drug concentration in plasma in rats when a mitomycin C-containing gel preparation prepared using a 1.5 W/V % aqueous solution of the galactose-partial degradation product or an aqueous mitomycin C solution was administered into the abdominal cavity of rats. The vertical axis represents the drug concentration in plasma ($\mu$g/ml), and the horizontal axis represents time (hour). The symbol —○— represents the case of administration of the control aqueous solution of mitomycin C, and the symbol —●— represents the case of administration of the mitomycin C-containing gel preparation prepared by using a 1.5 W/V % aqueous solution of the galactose-partial degradation product.
Figure 5:
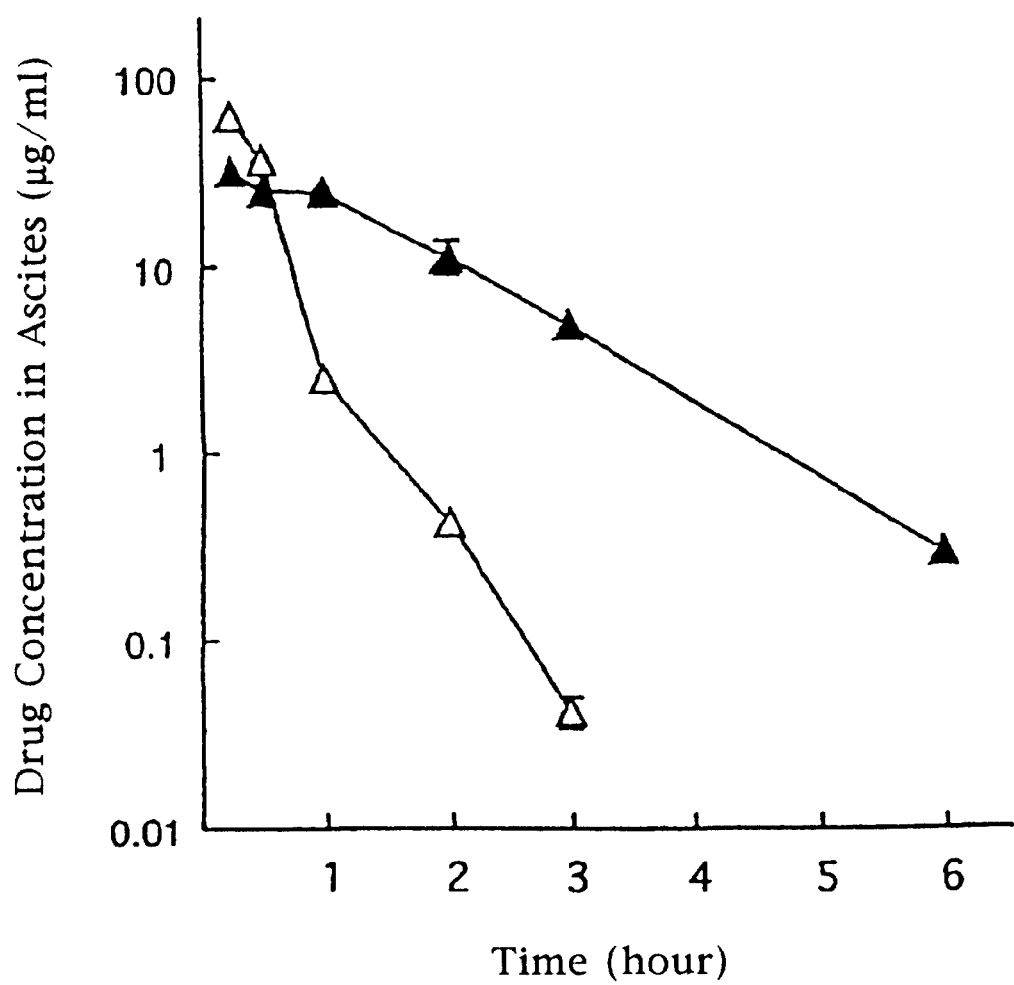
FIG. 5 shows the change of drug concentration in ascites in rats when a mitomycin C-containing gel preparation prepared using a 1.5 W/V % aqueous solution of the galactose-partial degradation product or an aqueous solution of mitomycin C was administered into the abdominal cavity of rats. The vertical axis represents the drug concentration in the ascites ($\mu$g/ml), and the horizontal axis represents time (hour). The symbol —△— represents the case of administration of the control aqueous solution of mitomycin C and the symbol —▲— represents the case of administration of the mitomycin C-containing gel preparation prepared by using the 1.5 W/V % aqueous solution of the galactose-partial degradation product.

As is shown in FIG. 4, in the case of administration of the control aqueous solution (—○—), blood concentration of the drug reached to the Cmax in 30 minutes after administration and thereafter reduced rapidly and after 3 hrs it was scarcely detected. On the other hand, in the case of administration of the gel preparation of the present invention (—●—), the drugs were transferred into the blood more slowly than the case of the control aqueous solution. Besides, as is clear from FIG. 5, in the case of administration of the gel preparation of the present invention (—▲—), the concentration of drugs in ascites was reduced more slowly than the case of administration of the control aqueous solution (—△—) and detected even after 6 hrs.

The above results suggest that an administration by infusion of the mitomycin C-containing gel preparation of the present invention enables to retain the drug in the abdominal cavity for a long time, and hence it is useful as a sustained release preparation.

INDUSTRIAL APPLICATION

The galactose-partial degradation product, which is produced by partial removal of galactose on the side-chain of a galactoxyloglucan with an enzyme (a removal ratio: 30~55%), exhibits thermally reversible gel characteristics, that is, it gels by heating (around a body temperature) and forms a sol by cooling, and hence, when the galactose-partial degradation product is used as a sustained release ingredient (as a gel base) for preparing a sustained release preparation, it is effective for duration of sustained release on the amount of drug released (eluted). Thus, it is very useful as a sustained release ingredient. Further, when the galactose-partial degradation product of the present invention is used for preparing tablets, the desired tablets having excellent sustained release properties can easily be prepared by tableting directly the mixture without using any carrier or diluent.

What is claimed is:

1. A pharmaceutical sustained release preparation comprising a partial degradation product of the galactose of a galactoxyloglucan, which is produced by subjecting a galactoxyloglucan originating from a plant to an enzymatic hydrolysis and to a galactose removal ratio of 30–55%, a pharmaceutically active compound and optionally a pharmaceutically acceptable carrier or diluent.

2. A pharmaceutical sustained release preparation according to claim 1, wherein the galactoxyloglucan is originated from a tamarind seed.

3. A pharmaceutical sustained release preparation according to claim 1, wherein the preparation is in a dosage form suitable for rectal or vaginal absorption, percutaneous or permucous membrane absorption, intraperitoneal administration or oral administration.

4. A pharmaceutical sustained release preparation according to claim 1, wherein the preparation is in the form of a suppository.

5. A method for sustained release of a pharmaceutically active compound, which comprises administering a pharmaceutical sustained release preparation comprising a partial degradation product of the galactose of a galactoxyloglucan, which is produced by subjecting a galactoxyloglucan originating from a plant to an enzymatic hydrolysis and to a galactose removal ratio of 30–55%, as a sustained release ingredient together with the pharmaceutically active compound and optionally a pharmaceutically acceptable carrier or diluent to a patient in need thereof.

6. A method according to claim 5, wherein the galactoxyloglucan is originated from a tamarind seed.

7. A method for making a pharmaceutical sustained release preparation, which comprises combining a partial degradation product of the galactose of galactoxyloglucan, which is produced by subjecting a galactoxyloglucan originating from a plant to an enzymatic hydrolysis and to a galactose removal ratio of 30–55%, as a sustained release ingredient with a pharmaceutically active compound and optionally a pharmaceutically acceptable carrier or diluent.

8. A method according to claim 7, wherein the partial degradation product of the galactose of a galactoxyloglucan is originated from a tamarind seed.

* * * * *